United States Patent [19]

Wiatr

[11] Patent Number: 5,071,765
[45] Date of Patent: Dec. 10, 1991

[54] APPLICATION OF MULTIPLE ENZYME BLEND TO CONTROL INDUSTRIAL SLIME ON EQUIPMENT SURFACES

[75] Inventor: Christopher L. Wiatr, Naperville, Ill.

[73] Assignee: Nalco Chemical Company, Naperville, Ill.

[21] Appl. No.: 322,804

[22] Filed: Mar. 13, 1989

[51] Int. Cl.$^5$ ............................................. B08B 17/00
[52] U.S. Cl. ..................................... 435/264; 435/262
[58] Field of Search ................................ 435/262, 264

[56] References Cited

U.S. PATENT DOCUMENTS 3,773,623 11/1973 Hatcher .
3,824,184 7/1974 Hatcher .
4,055,467 10/1977 Christensen .
4,684,469 8/1987 Pedersen .

OTHER PUBLICATIONS

Riedel et al., Chem. Abst., vol. 105 (1986), p. 213, 740q.
Blechschmidt et al., Chem. Abst., vol. 98 (1983), p. 2529b.
Wieg, Chem. Abst., vol. 100 (1984), p. 214,980b.

*Primary Examiner*—Sam Rosen
*Attorney, Agent, or Firm*—John S. Roberts, Jr.; Donald G. Epple

[57] ABSTRACT

A method of attacking and removing microbial slime in slime covered surfaces and maintaining a slime-free surface as in exposed cooling tower surfaces and in waste water treatment and paper making. This method comprises utilizing an enzyme blend in 2 to 100 parts per million (ppm) of beta-glucanase, alpha-amylase and protease. Such enzyme blends have been found specifically to digest microbial slime and reduce microbial attachment and biofilm. A specific combination of polysaccharide degrading enzymes is a ratio of 2 parts beta-glucanase to 1 alpha-amylase to 1 protease utilized in 2–100 parts per million. Broadly, the alpha-amylase must be at least 1 and the protease may vary from 0.5 to 1 part.

2 Claims, 6 Drawing Sheets

Biofilm Removal Reactor System

Microbial Fouling Reactor (MFR)

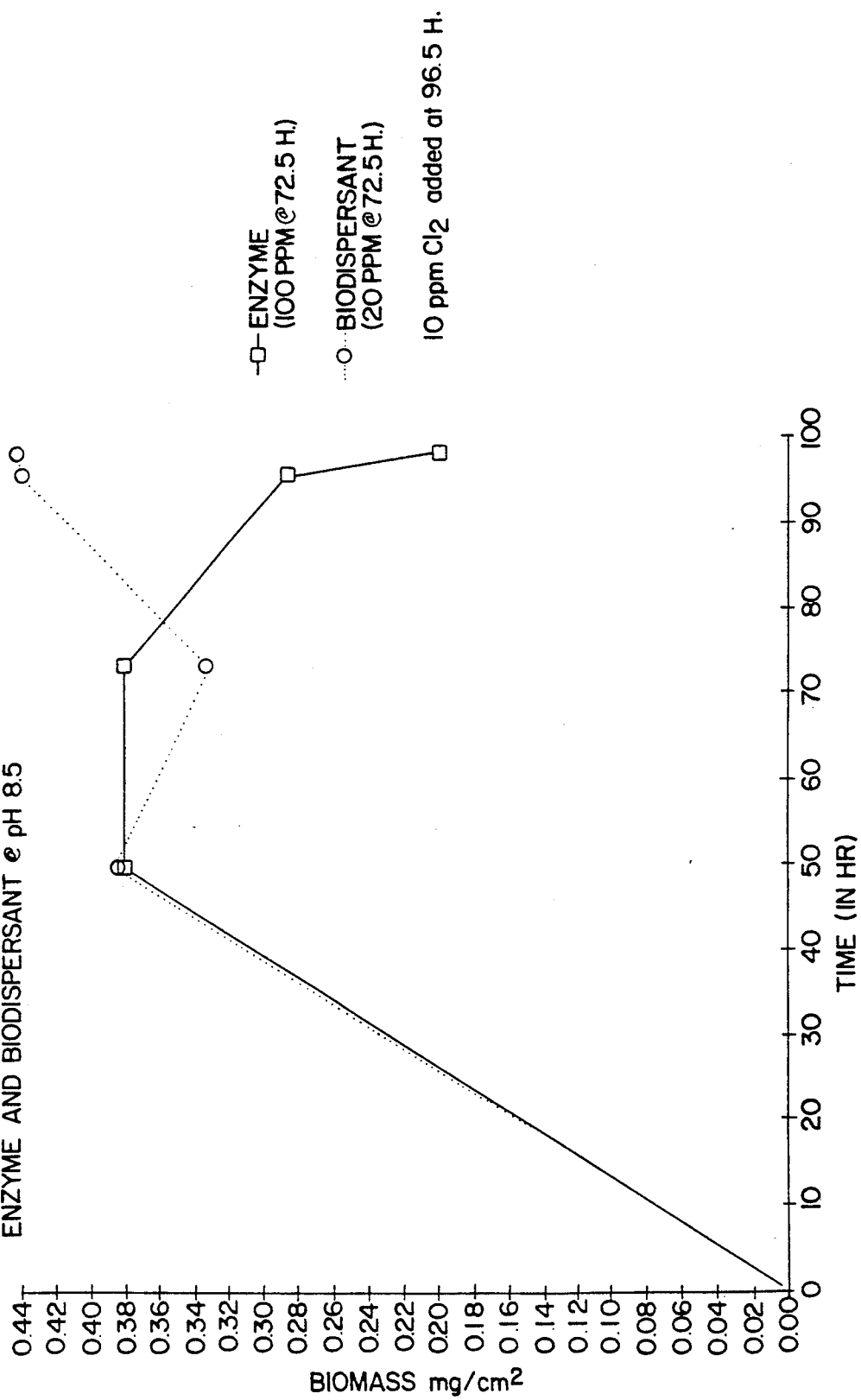

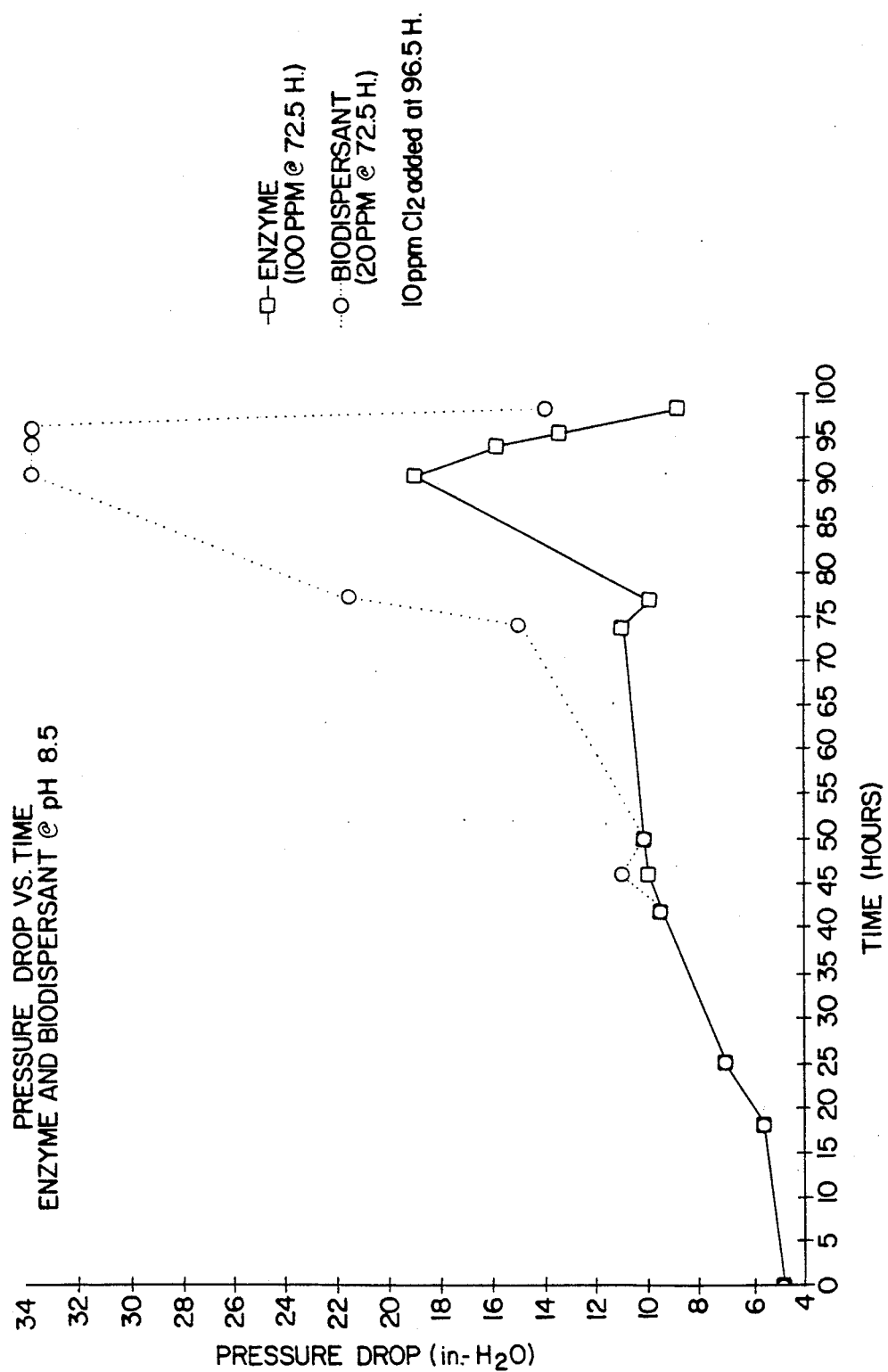

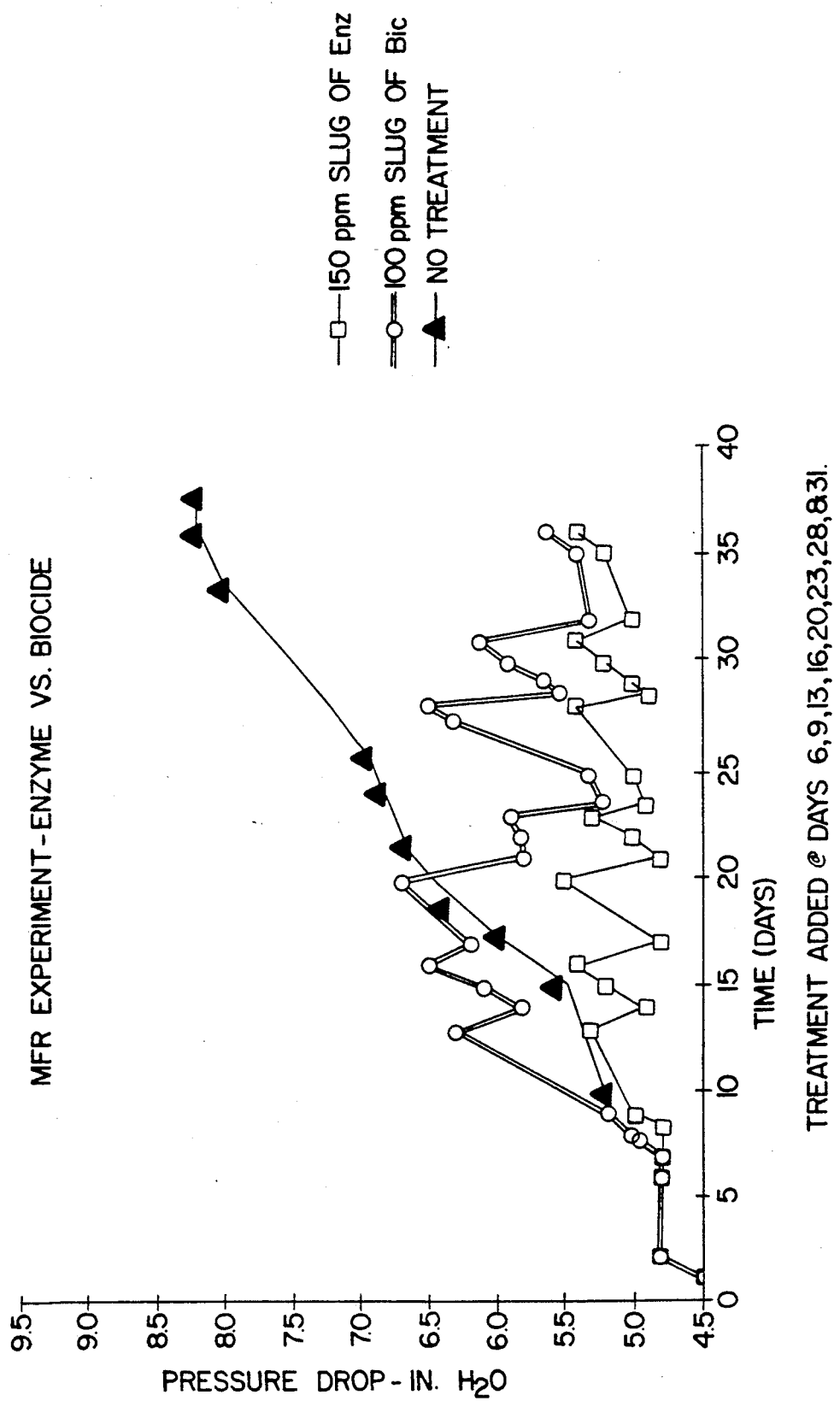

APPLICATION OF MULTIPLE ENZYME BLEND TO CONTROL INDUSTRIAL SLIME ON EQUIPMENT SURFACES

BACKGROUND OF THE INVENTION

The present invention relates to combined or composite enzyme systems for treating microbially produced extracellular polymers, present or which build up on surfaces of cooling water towers and in paper making broke water. Such extracellular polymers plus microbial cells are also known as biofilm or micorbial slime.

Microbially produced extracellular polymers can build up, retard heat transfer and restrict water flow through cooling water systems. Controlling slime-forming bacteria by applying toxic chemicals is becoming increasingly unacceptable due to environmental problems. In addition, the efficacy of the toxicants is minimized by the slime itself, since the extracellular polysaccharide eveloping micororganisms are largely impenetrable.

Toxicants cannot adequately control large populations of attached bacteria and they are effective mainly against floating microorganisms. Although surfactants and dispersants which penetrate and help loosen slime can enhance the activity of toxicants, they are nonspecific and may have deleterious effects on the industrial process.

This invention describes use of enzymes which have the advantage of being both specific and non-toxic. The approach is designed to (a) enchance the removal of slime where it has formed, (b) prevent the build-up of slime, and (c) improve the efficacy of biocides against sessile bacteria. The enzymes specifically attack the slime layer surrounding the bacteria. Consequently, the microorganisms become planktonic—harmless in terms of biofilm production—and are rendered susceptible to biocides. The enzymes also act to maintain a clean surface (see FIG. 6 and remarks). Examples of prior art single enzyme formulations are: those found in U.S. Pat. No. 3,773,623, Hatcher, Economics Laboratories, Inc., where the slime formulation in industrial water such as white water from pulp and paper mills is retarded by controlling amounts of enzyme levan hydrolase.

Also, U.S. Pat. No. 4,055,467, Christensen (Nalco) describes a slime and an industrial process whereby slime can be dispersed and prevented by treating said slime with a few ppm of the enzyme, Rhozyme HP-150, a pentosanase-hexosanase and U.S. Pat. No. 3,824,184, Hatcher (Economics Laboratories, Inc.) describes a slime formation controlled by intentionally adding to industrial water the controlled amounts of enzyme levan hydrolase.

Additionally, U.S. Pat. No. 4,684,469, Pedersen et al. (Accolab, Inc.) discloses a method of a two-component biocidal composition suitable for controlling slime. The preparation consists of a biocide and a polysaccharide degrading enzyme.

As to the biocides, generally methylene-bis-thiocyanate has been preferred. Other operable biocides includes chlorophenate compounds, such as pentachlorophenates and trichlorophenates; organomercurial compounds, such as phenylmercuric acid; carbamate compounds, such as methyldithiocarbamates, ethylenebisdithiocarbamates, and dimethyldithiocarbamates; carbonate compounds such as cyanodithioimidocarbonates; thiocyanates such as chloroethylene thiocyanate compounds; and other biocides such as bromohydroxyacetophenone compounds, benzothiazole compounds, ehtylene diamine compounds, nitrilopropionamides, bromopropionamides, bromo-acetoxybutenes, bromopropanolaldehyde compounds, bis-trichloromethyl sulfones, bimethyl hydantoin compounds, and the like mixtures of biocides can also be used.

The biocide methylene-bis-thiocyanate has proven to be particularly effective in the context of this invention, as has a combination of dimethyldithiocarbamate and disodium ethylenebisdithiocarbamate.

The advantages of the enzyme blend composition over the use of biocides to control bacteria are that the biocides constitute toxicants in the system and pollution problems are ever present The advantage of the present formulation over the formulation of a single enzyme plus biocide is that the single enzyme attacks only one narrow band of carbohydrate polymers whereas the present invention improves the range of attack by combining activities of a beta-glucanase and an alpha-amylase along with the basic protease, broadly attacking the carbohydrate polymer and protein surrounding the bacteria. A specific formulation embodying ratios, for the present use of multiple enzyme preparations, is 2 parts beta-glucanase, 1 part alpha-amylase, and 1 part protease. In this formulation, the alpha-amylase is at least 1 and can be slightly over 1 part. The protease which is set at 1 may actually be 0.5 to 1 part, the beta-glucanase is set at 2 parts.

A preferred composition is 2 parts beta-glucanase, 1 part alpha-amylase and 1 part protease. In the composition cerulase may be substituted for beta-glucanase.

In general, most enzymes are used in a dosage of 2 to 100 ppm and many are from 2 to 10 parts per million. The enzymes can be obtained from many chemical suppliers such as American Cyanamid, Betz, Beckman, Dearborn Chemical, Economics Laboratory, Inc., Merck, Nalco, Vineland Chemical, and the like.

The concentration of enzyme required for effectiveness in this invention varies greatly and can depend upon the conditions such as temperature and pH of the water, the microbial count and the type of industrial water being treated. The lower and upper limits of the required concentrations will substantially depend upon the specific enzyme or combination of enzymes used. For example, a highly effective enzyme can require a concentration of mainly about 1 or 2 parts enzyme to one million parts industrial water in the context of this invention, while another enzyme may require a minimum concentration of 80 or 100 ppm.

In contrast to the prior art, this formulation is both more specific and non-toxic. In view of this invention and in comparison with the prior art, it can be said that the present composition has the same over target polymers but digests them more efficiently because of the combined enzyme activities of alpha-amylase, beta-glucanase, and the protease. Moreover, the beta-glucanase is a unique enzyme component which allows this efficiency to take place. The alpha-amylase and the protease nick the microbial slime and allow the beta-glucanase access to digest the slime exopolymer more effectively.

. It is noted as a matter of general mechanisms, that the alpha-amylase alone does not give slime protection or remove slime. It attacks the alpha-linkage between glucose molecules. It nicks the outside of the slime molecule, so that the beta-glucanase can enter and attack said carbohydrate molecule. The protease attacks extracellular protein molecules.

Up to this time, enzyme treatment of industrial slime or slime polymer made by bacteria consisted of a single enzyme, for example levanase. Levanase would break down a polymer of levan into its subunits (fructose). However, after the levanase would be used on the slime levan, resistant bacteria would still remain to proliferate. Further applications of levanase were ineffective because the polymer it attacks was no longer present. The levan polymer would be gone, but other slime polymers would still be there and the bacteria would flourish. Although other enzyme preparations have been used in the marketplace, for example EDC, a levan hydrolyzer (Sunoco), there has been no combination of enzymes that would actually attack polymer made by Pseudomonas bacteria and other bacteria in the field, such as Klebsiella, Acinetobacter, Flavobacterium, Enterobacter, and Aerobacter, which were rich in glucose, mannose and gulose sugars arranged in polymers.

Now, in a generalized process and in response to the prior art above, the present invention has taken a clear culture of Pseudomonas bacteria and made them produce a slime polymer in a low substrate environment. Second, the invention has taken a composite of microorganisms from the field blended with and grown together both at the laboratory and under field conditions, simulated cooling tower water and utility water.

The results indicate that the maximum removal of carbohydrate layers from pending bacteria has occurred. Thus utilizing a new blend of enzymes has a superior result, especially if the enzyme utilization was found to be useful in the very prevalent Pseudomonas bacteria.

A variety of enzymes were utilized in testing against Pseudomonas bacteria. From 42 preparations of enzymes, three types of enzymes were found to be effective on slime produced by Pseudomonas bacteria. First, alpha-amylase was found to attack bacterial slime. Second, protease has been found also to have an effect on bacterial slime. Then it was found that a combination enzyme treatment with amylase, glucanase, and protease was effective in removing the biofilm. Neither one by themselves, however, would remove enough slime to be effective. The blend of glucanase, amylase and protease was the answer.

BRIEF DESCRIPTION OF THE DRAWINGS

FIG. 4 is a graph showing biofilm mass versus time for enzyme treatment and biodispersant.

FIG. 5 is a graph showing pressure drop versus time for enzyme treatement and biodispersant.

FIG. 6 is a graph showing the results of a treatment of enzyme versus biocide in a Microbial Fouling Reactor experiment.

EXAMPLES

EXAMPLE I

Preliminary activity screening of about forty enzyme candidates was carried out using slimed microscope slides which were treated with the enzyme candidates in small, stirred, sterile beakers. The test slides were prepared in a slime generation box using a colony isolate of Pseudomonas or a composite of field microorganisms known to produce extracellular polymers in industrial waters. Bacteria were propagated in tryptic soy broth (TSB) and were enumerated on tryptone glucose extract (TGE). Anhydrous dextrose (D-glucose) was used to supplement the TSB nutrient.

Enzyme digestion rates were determined at 1, 2 and 4-hour intervals by assessing biofilm removal from the slides visually. Enzyme candidates showing promising activity in this screening test were explored more fully as below.

EXAMPLE II

Figure 1:
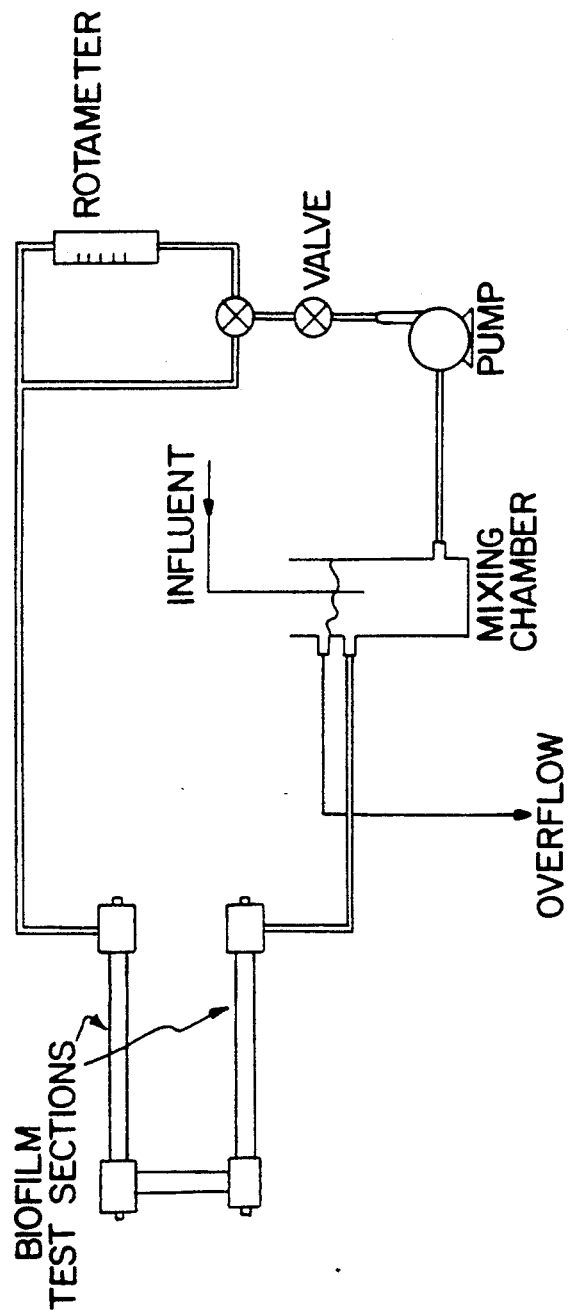
FIG. 1 is a plan view of the biofilm reactor system.

The nine most promising carbohydratases and proteases from the screening test were subjected to further examination using a Biofilm Removal Reactor (BRR) which simulates water-tube fouling in field applications. The reactor is shown schematically in FIG. 1. The reactor tubes were first slimed by exposure to slime-forming bacteria in circulated minimal substrate for a 72-hour period.

Figure 2:
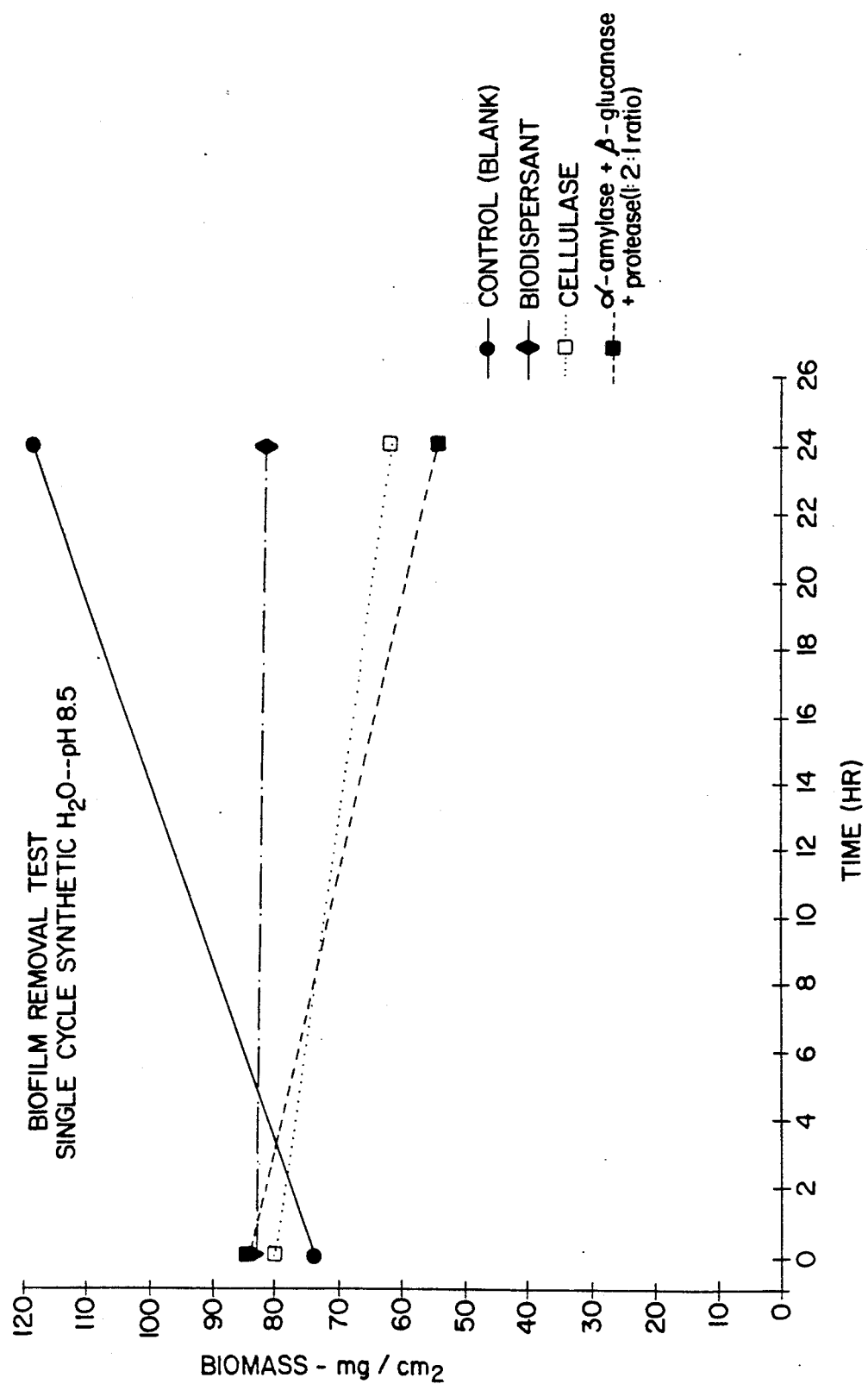
FIG. 2 is a graph indicating biofilm removal due to biodispersant, cellulase, and a mixture of alpha-amylase, beta-glucanase, protease in a 1:2:1 ratio.

Each of the candidate enzymes was tested in the reactor at a level of 100 ppm for a 24-hour period under the conditions shown in Table I. The removal of biofilm in the BRR was measured in terms of the percent decrease in biomass resulting from enzyme treatment of the fouled system. The results for the mixed protease-carbohydratase are shown in FIG. 2 and Table II. For these tests, the reactor tubes were dried overnight at 60 degrees C. and weighed; then cleaned, dried and reweighed to obtain the recorded gravimetric data.

Figure 3:
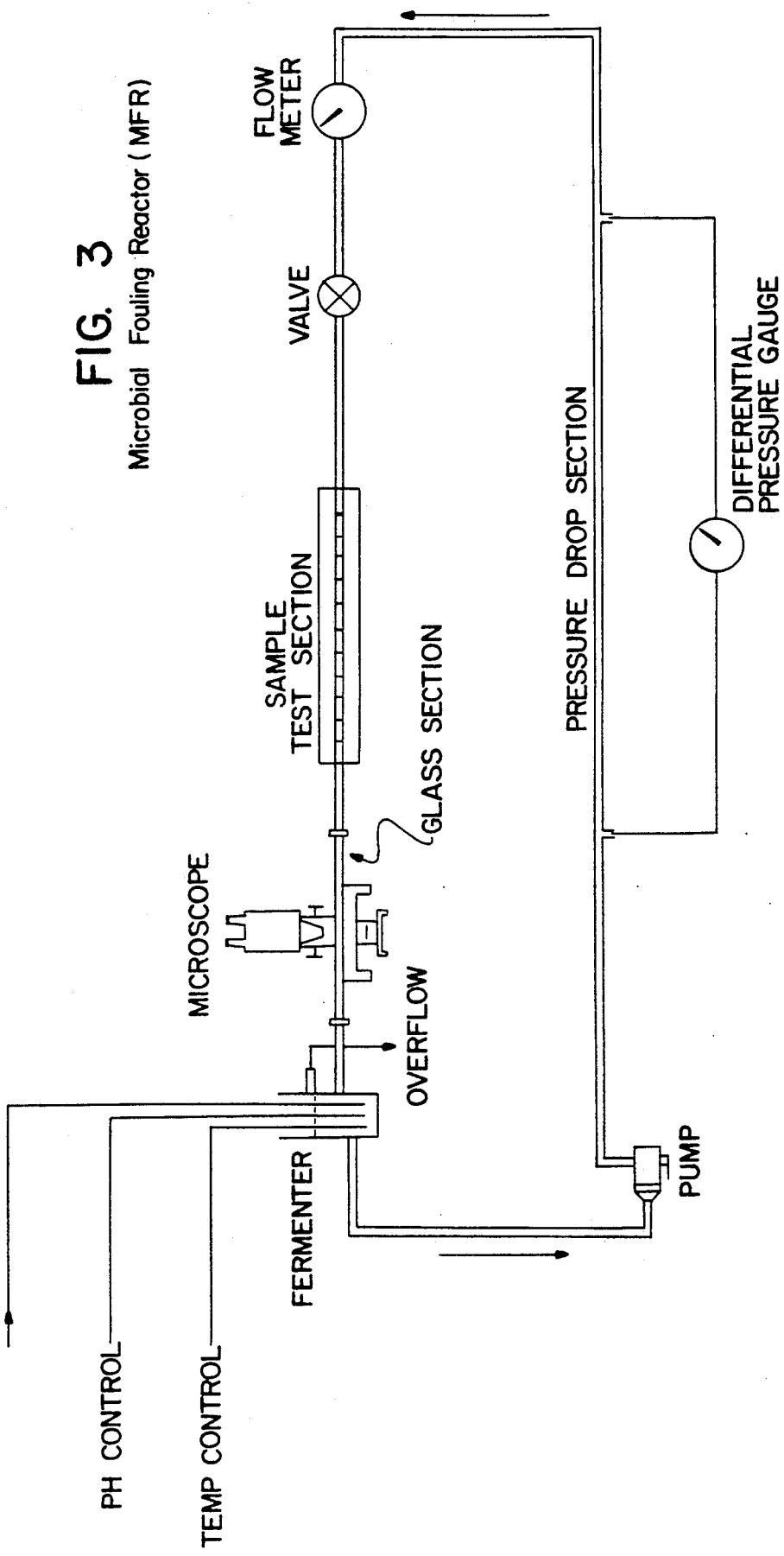
FIG. 3 is a plan view of the microbial fouling reactor system.

Further tests of these enzymes were conducted in a Microbial Fouling Reactor (MFR), a similar apparatus which also provides for a measure of pressure drop across the slimed reactor tubes as a criterion of fouling. The apparatus is shown in FIG. 3 and the experimental conditions are listed in Table I. The experimental procedure for the biomass measurements was generally similar to that used in BRR, above, except that the biomass is measured several times during the course of the experiment. In addition, the effectiveness of the enzyme treatment is measured by the decrease in pressure drop across the slimed tubes of the reactor as well as by visual observation in the sight glass section. FIGS. 4 and 5 show the results of tests of the mixed enzyme compared to a polyol biodispersant.

Five of the enzyme preparations tested in the Biofilm Removal Reactor were effective in controlling slime. These are tabulated in Table II with their relative effectiveness. Of these, the mixed enzyme was clearly the best performer. This enzyme composite is a combination of one protease and two carbohydratases, namely alpha-amylase and beta-glucanase. It was found to be effective in digesting slime layers produced by cultures of pure and mixed strains of bacteria. One commercially available mixed enzyme composition is shown in the table to give 37% biomass removal in the time period of the test.

The Biofilm Removal Reactor (FIG. 1) results are also depicted in FIG. 2. In the biofilm removal experiments, the enzyme cellulase removed 23% of the biomass (62 mg/cm$^2$ after treatment as opposed to 80 mg/cm$^2$ before treatment) in 24 hours. The 1:2:1 combination of alpha-amylase, beta-glucanase, and protease enzymes removed 37% of the biofilm in the same time frame. The control (blank), which was untreated, continued to increase in biomass 65%. For comparison, a non-enzymatic chemical biodispersant essentially checked overall development of biofilm but did not remove any biomass. Therefore, the multiple enzyme approach was the best (37%).

The biomass removal results in the MFR experiment agreed essentially with 37% removal between 72.5 and 96.5 hr (FIG. 4). The pressure drop data (FIG. 5) in the same (MFR) experiment support this finding.

EXAMPLE III

Focusing on the mixed enzyme, further MFR studies were conducted to determine the effect of pH on its effectiveness in biofilm removal. The composite enzyme was tested using a polyol biodispersant as a control in single-cycle synthetic tap water with pH maintained at 7.5, 8.5 or 9.0. The results are summarized in Table III. The mixed enzyme was effective up to pH 9. The efficacy of the enzyme combination is also compared to that of the dispersant at neutral and alkaline pH's in Table III.

Example IV

An experiment was run on the Microbial Fouling Reactor and the results are shown in FIG. 6. The experiment was designed to test whether the enzyme product of this invention would keep a surface clean. The conditions for the experiment differed in substrate concentration and treatment dosage (Table IV). The substrate concentration was low, similar to substrate level in cooling water. The dose was either slug of biocide or enzyme product.

In FIG. 6, the control or no treatment (—▲—) curve indicates what biofilm growth is possible in low substrate conditions. The biocide curve indicates 100 ppm nonoxidizing biocide slugged in the reactor at days 6, 9, 13, 16, 20, 23, 28 and 31 caused losses in biofilm, as measured by decreases in pressure drop. The curve representing performance of the enzyme combination also indicates biofilm loss after each treatment. After 31 days the difference between the biocide-treated line and the untreated control was 2.4 inches (Δp=2.4 in.); 2.7 inches using the enzyme blend. FIG. 6 indicates that after treatments were stopped, the biofilm in both lines grew.

The results were good. The experiment demonstrated that the enzymes controlled the biofilm growth very well over one month. The enzyme blend, which is non-toxic, performed at least as well as the toxicant (nonoxidizing) biocides.

In the specification and claims, glucanase is equivalent and equal to beta-glucanase.

TABLE I

| | Biofilm Removal Test Conditions | |
|---|---|---|
| | Conditions Per Apparatus | |
| Parameter | BRR | MFR |
| pH | 8.5 | 7.5, 8.5 or 9.0[a] |
| Temperature (°C.) | 36 ± 1[b] | 33.0 ± 1[c] |
| Make-up Water | Synthetic Chicago Tap[d] | Synthetic Chicago Tap[d] |
| Substrate Concentration | | |
| TSB | 50 ppm | 50 ppm |
| D-glucose | 50 ppm | 50 ppm |
| Inoculum | Field Composite | Field Composite |
| Growth Period | 72 Hr | p ≦ 10 in[e] |
| Treatment | | |
| Enzyme Concentration | 100 ppm | 100 ppm |
| Duration | 24 Hr | 24 Hr |

[a]pH setting depended on experiment.
[b]BRR temperature is consistently 36° ± 1° C. resulting from operation of recirculating pump.
[c]MFR temperature is thermostatically controlled.
[d]Single cycle synthetic Chicago tap.
[e]MFR p of 10 inches occurred at approximately 72 Hr.

TABLE II

| Summary of BRR Studies at pH 8.5 | |
|---|---|
| Type of Enzyme | % Removal |
| Neutral Protease | −10.0 |
| Alkaline Protease(1) | −50.0 |
| Alkaline Protease(2) | 18.0 |
| Debranching Enzyme | −19.0 |
| Alkaline alpha-amylase | 21.5 |
| Beta-glucanase(1) | 0 |
| Beta-glucanase(2) | 14.0 |
| Cellulase[a] | 23.0 |
| Alpha-amylase, Beta-glucanase + Protease[b] | 37.0 |

[a]Cellulase attacks the beta-linkage between sugar molecules.
[b]Alpha-amylase, beta-glucanase and neutral protease activities.

TABLE III

| Effect of pH on Enzyme Treatment Performance[a] | | |
|---|---|---|
| | % Removal of Biofilm[b] | |
| pH | Enzyme | Biodispersant |
| 7.5 | 48 | 3 |
| 8.5 | 35[b] | 1[b] |
| 9.0 | 44[b] | 11[b] |

[a]Performance is evaluated at 100 ppm enzyme, 20 ppm biodispersant concentration levels.
[b]Removal is an average of two experiments at 33 ± 1° C.

TABLE IV

| Microbial Fouling Reactor Test Conditions for Biofilm Control Experiment | |
|---|---|
| Parameter | Conditions |
| pH | 8.5 |
| Temperature | 33.0 ± 1.0° C. |
| Make-up Water | Synthetic Tap Water |
| Substrate Concentration | |
| TSB | 10 ppm |
| D-glucose | 10 ppm |
| Inoculum | Field Composite |
| Treatments | |
| Enzyme Concentration | 150 ppm |
| Duration | Slug dose |
| Frequency | Twice per week |
| Biocide Concentration | 100 ppm |
| Duration | Slug dose |
| Frequency | Twice per week |

And we claim:

1. A method of removing and preventing buildup of microbial slime on the surface of industrial water treatment equipment in contact with industrial water containing slime-forming bacteria, which method comprises contacting said microbial slime on said surface of industrial water treatment equipment with a composite enzyme system containing beta-glucanase, alpha amylase and protease.

2. A method of removing and preventing buildup of microbial slime of the surface of cooling tower in contact with cooling tower water containing slime-forming bacteria, which method comprises contacting said microbial slime on said surface of industrial water treatment equipment with a composite enzyme system containing beta-glucanase, alpha amylase and protease.

* * * * *